United States Patent [19]

Arnaud et al.

[11] Patent Number: 4,593,101
[45] Date of Patent: Jun. 3, 1986

[54] PROCESS FOR THE PREPARATION OF 4-QUINOLINONES

[75] Inventors: Michel Arnaud, Salindres; Jean-Pierre Corbet, Ecully, both of France

[73] Assignee: Rhone-Poulenc Sante, Courbevoie, France

[21] Appl. No.: 652,527

[22] Filed: Sep. 20, 1984

[30] Foreign Application Priority Data

Sep. 22, 1983 [FR] France ............................ 83 15073

[51] Int. Cl.[4] ................... C07D 215/18; C07D 215/22
[52] U.S. Cl. ..................................... 546/153; 564/442; 560/43
[58] Field of Search ........................................ 546/153

[56] References Cited

PUBLICATIONS

Johnson–J. Amer. Chem. Soc. 71, pp. 1901–1905 (1949).
Elderfield, J. Amer. Chem. Soc. 68, pp. 1259–1263 (1946).
Hashimoto, CA: 86: 190461x (1977).
Green, "Protective Groups in Organic Synthesis", pp. 250, 251, 285.

Primary Examiner—Donald G. Daus
Assistant Examiner—Robert Benson
Attorney, Agent, or Firm—Stevens, Davis, Miller & Mosher

[57] ABSTRACT

1,2,3,4-Tetrahydro-4-quinolinone of formula:

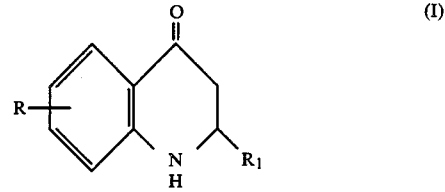

are prepared from a 3-anilinopropionic acid of formula:

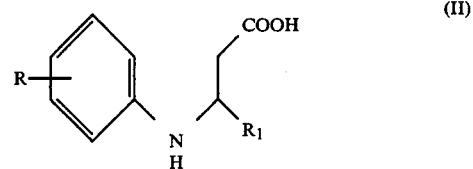

which is treated successively with phosgene, phosgene in the presence of dimethylformamide, a Lewis acid or a strong acid, and a base. In the formula (I) and (II), R denotes a hydrogen atom, a halogen atom or an alkyl (1 to 4 carbon atoms) or alkoxy (1 to 4 carbon atoms) radical, and $R_1$ denotes a hydrogen atom or an alkyl radical (1 to 4 carbon atoms). The compounds of formula I are useful as intermediates in the production of known drugs.

7 Claims, No Drawings

PROCESS FOR THE PREPARATION OF 4-QUINOLINONES

The present invention relates to the preparation of 1,2,3,4-tetrahydro-4-quinolinones of the formula:

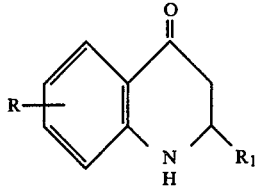

in which R denotes a hydrogen atom, a halogen atom, a linear or branched alkyl radical of 1 to 4 carbon atoms or a linear or branched alkoxy radical of 1 to 4 carbon atoms, and $R_1$ denotes a hydrogen atom or a linear or branched alkyl radical of 1 to 4 carbon atoms. These compounds are especially useful as intermediates in the synthesis of therapeutically active substances.

It is known that 1,2,3,4-tetrahydro-4-quinolinones of general formula (I) can be prepared by cyclisation of a 3-anilinopropionic acid with polyphosphoric acid according to the process described in French Patent No. 1,514,280, with an oleum according to the process described in European Patent No. EP 56,764 or with a hydrofluoric acid/boron trifluoride mixture according to the process described in European Patent EP No. 56,763.

It should, however, be noted that, in the particular case of the cyclisation of 3-(m-chloroanilino)-propionic acid by polyphosphoric acid, a mixture of substantially equal quantities of 5-chloro- and 7-chloro-1,2,3,4-tetrahydro-4-quinolinone is obtained. The selectivity for 7-chloro-1,2,3,4-tetrahydro-4-quinolinone is significantly improved if an oleum or a hydrofluoric acid/boron trifluoride mixture is used as cyclisation agent, but the industrial use of these processes encounters difficulties which result either from the handling of large quantities of sulphuric acid or from the utilisation of a mixture of anhydrous hydrofluoric acid and boron trifluoride.

It has now been found, and this is the subject of the present invention, that the products of general formula (I) can be obtained in good yields and, when the case arises, with increased selectivity, from 3-anilinopropionic acids by carrying out reactions which are simpler than, and have the same high performance as, those previously known.

According to the invention, a 3-anilinopropionic acid of the formula:

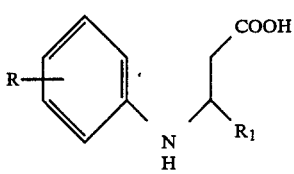

in which R and $R_1$ are defined as above, is treated with phosgene to produce a product of the formula:

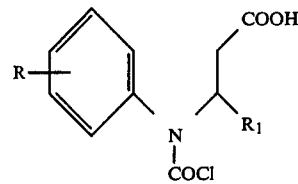

in which R and $R_1$ are as defined above, the compound of formula (III) is then converted by the action of phosgene in the presence of dimethylformamide, into the acid chloride of the formula:

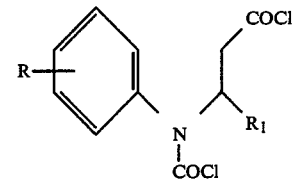

in which R and $R_1$ are as defined above, and the compound of formula IV is then cyclized, by the action of a Lewis acid in a suitable solvent or a strong acid, to give a product of the formula:

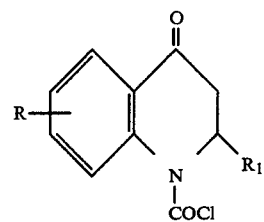

in which R and $R_1$ are as defined above, which is then hydrolysed by the action of a base to give a product of formula (I).

The compounds of formula (III) are preferably obtained by the action of phosgene on a compound of formula (II) in an organic solvent such as methylene chloride, 1,1,2-trichloroethane, an aliphatic ester or dioxane, at a temperature between $-10°$ and $150°$ C., and preferably between $30°$ and $80°$ C. Generally, a slight excess of phosgene (less than 10%) is employed relative to the 3-anilinopropionic acid of formula (II) used. It is advantageous to work in an inert atmosphere.

The compounds of formula (IV) are preferably obtained by the action of phosgene on a compound of formula (III) in the presence of a trace of dimethylformamide, working in an organic solvent such as methylene chloride, a trihalogenoethane such as 1,1,2-trichloroethane or dioxane, at a temperature between $-10°$ and $100°$ C., and preferably between $0°$ and $50°$ C. Generally, a slight excess of phosgene (less than 10%) is used relative to the product of general formula (III). It is advantageous to work in an inert atmosphere.

The compounds of the formula (V) are preferably obtained by intramolecular cyclisation of a product of general formula (IV) with a Lewis acid or a strong acid. Suitable Lewis acids include aluminum chloride, ferric chloride, titanium chloride and stannic chloride. Preferred strong acids, are sulphuric acid, hyrofluoric acid, sulphonic acids (e.g. alkylsulphonic, arylsulphonic, and trifluoromethanesulphonic acids) and polyphosphoric acid.

When a Lewis acid is used, the reaction is carried out in a suitable solvent at a temperature between −10° and 70° C. and preferably between 0° and 50° C. The organic solvent may be a halogenated hydrocarbon such as methylene chloride, a trihalogenoethane such such as 1,1,2-trichloroethane, carbon disulphide, a nitroalkane or tetrachloroethylene.

When a strong acid is used, cyclisation is performed at a temperature between 20° and 100° C.

The products of formula (V) can also be obtained directly from a 3-anilinopropionic acid without the need for the intermediate isolation of the compounds of formula (III) and (IV).

For this purpose, the product of general formula (II) is treated with phosgene in the proportion of at least 2 moles of phosgene per mole of 3-anilinopropionic acid of general formula (II) used, in an organic solvent such as methylene chloride or 1,1,2-trichloroethane at a temperature between −10° and 150° C. and preferably between 30° and 80° C., dimethylformamide is then added and the reaction is continued until conversion is complete. After removal of the excess of phosgene, the Lewis acid or the strong acid is added to the reaction mixture and the reaction is continued until the starting material and intermediate products have completely disappeared. When the reaction has finished, the product of general formula (V) is separated from the reaction mixture by the customary methods.

The products of formula (I) can be obtained by the action of an inorganic base on a product of formula (V). It is especially advantageous to use caustic soda in methanol solution while working at a temperature between 50° and 100° C.

The products of formula (I) can be isolated from the reaction mixture and purified by the customary methods.

The products of formula (IV) and the products of formula (V), with the exception of those in which $R_1$ denotes a hydrogen atom and R denotes a chlorine, bromine or fluorine atom in position 6, are new compounds which constitute another subject of the present invention.

The acids of formula (II) used as starting material can be obtained by the action of a suitably substituted aniline on an acid of formula:

$$R_1—CH=CH—COOH \quad (VI)$$

in which $R_1$ is defined as above. The reaction is generally performed in water at a temperature between 70° and 100° C., employing an excess of aniline relative to the acid of formula (VI) used. The reaction time is generally between 1 and 4 hours.

The 1,2,3,4-tetrahydro-4-quinolinones of general formula (I) are especially useful as intermediates in the synthesis of therapeutically active substances such as chloroquine, glafenine, antrafenine or amodiaquine. More especially, 7-chloro-1,2,3,4-tetrahydro-4-quinolinone can be converted to chloroquine by condensation with 4-diethylamino-1-methylbutylamine in the presence of air according to the process described by W. S. Johnson and B. G. Buell, J. Amer. Chem. Soc., 74, 4513 (1952).

The Examples which follow show how the invention can be put into practice.

EXAMPLE 1

In a 100 cc round-bottomed flask equipped with magnetic stirring, a thermometer, an acetone/dry ice reflux condenser, a device for introducing gas and a dropping funnel, dry methylene chloride (20 cc) is introduced. Phosgene (3.15 g; 31.8 mmol) is condensed in at a temperature between 0° and 5° C. The reaction mixture is maintained under an atmosphere of argon. There is then introduced, in the course of 19 minutes, a solution of 3-(m-chloroanilino)propionic acid (6.25 g; 31.3 mmol) in methylene chloride (15 cc). The temperature rises from 6° to 23° C. The reaction mixture then consists of a yellow liquid phase and a white precipitate in suspension. The stirring is continued for 10 minutes at 23° C. and then a stream of argon is passed through the reaction mixture for 50 minutes to remove the phosgene which has not reacted.

The precipitate is separated by filtration under a stream of argon and then dried to constant weight under reduced pressure (1 mm Hg; 0.13 kPa). 3-(m-Chloroanilino)propionic acid hydrochloride (3.2 g) is thus obtained.

The filtrate is concentrated to dryness. N-Chloroformyl-3-(m-chloroanilino)propionic acid (4.58 g) is thus obtained almost pure, m.p. 106° C., the structure of which is confirmed by the infrared spectrum, mass spectrum and proton nuclear magnetic resonance spectrum. The product after recrystallisation in isopropyl ether melts at 111° C.

3-(m-Chloroanilino)propionic acid can be prepared in the following manner:

To a mixture of m-chloroaniline (510.3 g) in water (150 cc) maintained under an atmosphere of argon and stirred at 80° C., there is added, in the course of 10 minutes, a solution of acrylic acid (72.05 g) in water (100 cc). The reaction mixture, which consists of two phases, is maintained for 3 hours at 80° C. with stirring, and is then cooled to 20° C. After decantation, the aqueous phase (upper layer) is removed. A 2.6N aqueous caustic soda solution (423 cc) is added to the organic phase while it is stirred, the temperature being maintained at 20° C. After decantation, the organic phase consisting of m-chloroaniline (303 g) is separated. The aqueous phase (850 cc) is extracted successively with ether (6×450 cc).

The aqueous phase, from which the ether is removed by evaporation under reduced pressure (20 mm Hg; 2.7 kPa), is acidified by adding 50% strength (by weight) sulphuric acid (105 g). The final pH is 3.5 (isoelectric point). The temperature changes from 22° to 33° C., and the mixture is then heated to 40° C. After decantation, the following are separated:

a lower organic phase (208.8 g) consisting of melted 3-(m-chloroanilino)propionic acid saturated with water (8.6% of water)

an upper aqueous phase (601 g) containing 3-m-(chloroanilino)propionic acid (2.28 g) and sodium sulphate (156 g).

The organic phase is heated for 1 hour to 80° C. under reduced pressure (20 mm Hg; 2.7 kPa). A product (195.4 g) is obtained which contains 3-(m-chloroanilino)propionic acid (94%) and water (2.3%).

EXAMPLE 2

In an apparatus identical to that used in Example 1, dry methylene chloride (30 cc) and dimethylformamide (0.2 cc) are introduced. Phosgene (3.2 g; 32.35 mmol) is then condensed in at a temperature in the region of 5° C. During the condensation a light white precipitate is formed. The temperature is allowed to rise to about 16° C. and a solution of N-chloroformyl-3-(m-chloroanilino)propionic acid (7.06 g; 26.93 mmol) in dry methylene chloride (50 cc) is then added. The precipitate gradually dissolves and at the end of the addition the reaction mixture is yellow and clear. The temperature of the reaction mixture is 27° C. The excess of phosgene is removed by bubbling a stream of argon through the reaction mixture for 30 minutes and the mixture is then left to stand for 15 hours at a temperature in the region of 20° C.

The reaction mixture is concentrated under reduced pressure (20 mm Hg; 2.7 kPa) at 40° C. A yellow-orange oil (8 g) is thus obtained. This oil is taken up in ethyl acetate (20 cc) at 4° C. A light precipitate is formed which is separated by filtration under an atmosphere of argon. The filtrate is concentrated to dryness under reduced pressure (20 mm Hg; 2.7 kPa) and then dried to constant weight under reduced pressure (1 mm Hg; 0.13 kPa) at 40° C. N-Chloroformyl-3-(m-chloroanilino)propionic acid chloride (7.4 g) is thus obtained almost pure in the form of an orange oil, the structure of which is confirmed by quantitative elementary analysis, the infrared spectrum, mass spectrum and proton nuclear magnetic resonance spectrum.

EXAMPLE 3

In an apparatus idenntical to that used in Example 1, methylene chloride (25 cc) is introduced. A stream of phosgene is then passed through for 10 minutes at a temperature in the region of 20° C., in order to remove the water and ethanol present in the solvent used. The phosgene dissolved is removed by passing a stream of argon through the solution for 20 minutes at a temperature in the region of 40° C. N-Chloroformyl-3-(m-chloroanilino)propionic acid chloride (2 g; 7.13 mmol) is then added, while working under an atmosphere of argon at a temperature of 26° C. Anhydrous aluminum chloride (2.09 g) is then added in the course of 10 minutes, the temperature changing from 26° to 32° C. The reaction mixture then consists of a yellow liquid phase and a suspension. The mixture is left to react for 15 hours at a temperature in the region of 20° C., and the reaction mixture is then poured onto ice (25 g). The organic phase is separated by decantation. The aqueous phase is extracted with methylene chloride (4×25 cc). The combined organic extracts are washed with water (4×25 cc) and then dried over sodium sulphate. After filtration, the filtrate is concentrated to dryness under reduced pressure (20 mm Hg; 2.7 kPa) at 40° C. 1-Chloroformyl-7-chloro-1,2,3,4-tetrahydro-4-quinolinone (1.5 g), m.p. 150°–153° C., is thus obtained which, after recrystallisation in ethyl acetate, melts at 156° C.

The structure of the 1-chloroformyl-7-chloro-1,2,3,4-tetrahydro-4-quinolinone is confirmed by its quantitative elementary analysis, its infrared spectrum, mass spectrum and proton nuclear magnetic resonance spectrum.

EXAMPLE 4

1-Chloroformyl-7-chloro-1,2,3,4-tetrahydro-4-quinolinone (0.5 g; 2.05 mmol) is introduced into a normal solution (20 cc) of caustic soda in methanol. The mixture is heated to 65° C. for 3 hours 10 minutes. The reaction mixture is concentrated under reduced pressure (20 mm Hg; 2.7 kPa) at 40° C. and then taken up in water (100 cc) and methylene chloride (100 cc). After decantation, the aqueous phase is extracted with methylene chloride (3×50 cc). The combined organic phases are washed with distilled water (4×50 cc) and then dried over sodium sulphate. After filtration and concentration to dryness, 7-chloro-1,2,3,4-tetrahydro-4-quinolinone (0.36 g), m.p. 132° C., is obtained.

Analysis of this product by gas chromatography shows that it contains 7-chloro-1,2,3,4-tetrahydro-4-quinolinone (91%).

EXAMPLE 5

Dry methylene chloride (20 cc) is introduced into an apparatus identical to that described in Example 1. Phosgene (7.85 g; 79.37 mmol) is then condensed in at between 4° and 5° C., and a solution of 3-(m-chloroanilino)propionic acid (5.946 g; 29.81 mmol) in methylene chloride (12 cc) is then added in the course of 15 minutes. During the addition, the temperature of the reaction mixture rises from 7° to 17° C. and a copious beige precipitate forms. The mixture is then heated to 30° C. for 30 minutes. After cooling the mixture to 25° C., dry dimethylformamide (0.1 cc) is added by means of a syringe. A steady evolution of gas occurs which slows down after 30 minutes. Dimethylformamide (0.1 cc) is then added again: the evolution of gas resumes. After 1 hour, the initial precipitate is completely dissolved. The complete disappearance of the starting material is confirmed by thin layer chromatography. The reaction mixture is heated to 38° C. and a stream of argon is passed through it to remove the excess of phosgene which has not reacted.

After the mixture has cooled to 20° C., anhydrous aluminum chloride (8.49 g; 63.66 mmol) is added in the course of 40 minutes. The mixture is left to react at a temperature in the region of 20° C. for 23 hours 45 minutes.

The reaction mixture is poured onto ice (150 g). The aqueous phase is extracted with methylene chloride (4×50 cc) and the combined organic phases are washed with water (5×30 cc) and then dried over anhydrous sodium sulphate. After filtration, and concentration of the filtrate to dryness under reduced pressure (20 mm Hg; 2.7 kPa) at 40° C., 1-chloroformyl-7-chloro-1,2,3,4-tetrahydro-4-quinolinone (7.294 g) is obtained almost pure in the form of a yellow solid.

1-Chloroformyl-7-chloro-1,2,3,4-tetrahydro-4-quinolinone (477.7 mg) is treated with a normal solution of caustic soda in methanol under the conditions described in Example 4. A pale yellow solid (363.4 mg) is thus obtained, analysis of which by gas chromatography and by high performance liquid chromatography shows that it contains 7-chloro-1,2,3,4-tetrahydro-4-quinolinone (89%) and 5-chloro-1,2,3,4-tetrahydro-4-quinolinone (0.5%).

The yield of 7-chloro-1,2,3,4-tetrahydro-4-quinolinone is 91.2% relative to the 3-(m-chloroanilino)propionic acid used.

EXAMPLE 6

To a solution of N-chloroformyl-3-(m-chloroanilino)propionic acid chloride (1.37 g; 4.90 mmol) in methylene chloride (5.7 cc), prepared in a manner identical to that described in Example 2, titanium tetrachloride (2.04 g; 10.77 mmol) is added in the course of 10 minutes at a temperature in the region of 20° C. The reaction mixture is stirred at this temperature for 20 hours and then at a temperature in the region of 40° C. for 4 hours 30 minutes. After being cooled to a temperature in the region of 20° C., the reaction mixture is poured onto ice (25 g). The organic phase is separated by decantation. The aqueous phase is extracted with methylene chloride (4×15 cc). The combined organic extracts are washed with water (2×20 cc) and then dried over sodium sulphate. After filtration, the filtrate is concentrated to dryness under reduced pressure (20 mm Hg; 2.7 kPa) at 40° C. A brown residue (1.195 g) is then obtained which essentially contains 1-chloroformyl-7-chloro-1,2,3,4-tetrahydro-4-quinolinone.

A part of this residue (0.460 g) is treated with a 1N solution (20 cc) of caustic soda in methanol in a manner identical to that described in Example 4. A brown residue (0.170 g) is thus obtained.

Analysis of this residue by gas chromatography shows that it contains 7-chloro-1,2,3,4-tetrahydro-4-quinolinone (81.5%).

The yield is 40.5% relative to the 3-(m-chloroanilino)propionic acid used.

EXAMPLE 7

In a stainless steel reactor containing a solution of N-chloroformyl-3-(m-chloroanilino)propionic acid chloride (1.26 g; 4.5 mmol) in methylene chloride (5 cc) cooled to 0° C., anhydrous hydrofluoric acid (20.0 g) is introduced. The reactor is then closed and then heated to 80° C. for 17 hours 25 minutes. The internal pressure is approximately 6 bars. The reactor is then cooled to 10° C. and the liquid is poured onto a mixture of water and ice (100 g in total). After extraction with methylene chloride (3×30 cc), the combined organic extracts are washed with a potassium carbonate solution (70 cc) and then with distilled water (2×50 cc) and are finally dried over sodium sulphate. After filtration and concentration to dryness under reduced pressure (20 mm Hg; 2.7 kPa), an oily residue (0.75 g) is obtained.

This residue is treated with a normal solution (30 cc) of caustic soda in methanol in a manner identical to that described in Example 4. A yellow semi-crystalline residue (0.40 g) is thus obtained.

Analysis of this residue by gas chromatography shows that it contains 7-chloro-1,2,3,4-tetrahydro-4-quinolinone (77.9%).

The yield is 38.2% relative to the 3-(m-chloroanilino)propionic acid chloride introduced.

EXAMPLE 8

In an apparatus identical to that described in Example 1, 3-(2-methylanilino)propionic acid (6.27 g; 35.0 mmol) and dry methylene chloride (38 cc) are introduced. The reaction mixture is maintained in the region of 40° C. and phosgene (9.35 g; 94.5 mmol) is introduced in the course of 37 minutes. During this addition, a white precipitation is formed. Dry dimethylformamide (0.25 g; 3.4 mmol) is added by means of a syringe at a temperature in the region of 35° C. Evolution of a gas takes place which ceases after approximately one hour, while the temperature of the reaction mixture is maintained at between 35° and 40° C. A stream of argon is then passed through to drive out the excess of phosgene which has not reacted.

After the mixture has been cooled to about 20° C., aluminum chloride (11.29 g; 84.7 mmol) is added in the course of 6 minutes. The mixture is left to react at a temperature in the region of 20° C. for 18 hours 45 minutes.

The reaction mixture is then treated in a manner similar to that described in Example 5. A yellow product (7.83 g; 35.0 mmol), m.p. 99° C., is thus obtained. Spectral analysis of this product shows that it is almost pure 1-chloroformyl-8-methyl-1,2,3,4-tetrahydro-4-quinolinone. After recrystallisation in hexane, the product melts at 108° C.

3-(2-Methylanilino)propionic acid is prepared in a manner similar to that described in Example 1, but starting from o-toluidine (64.3 g; 0.60 mol), acrylic acid (11.6 g; 0.16 mol) and water (36.6 cc). A white powder (23.85 g) is thus obtained which, after recrystallisation in a toluene/hexane mixture (70:30 by volume), gives a pure product (21.7 g; 0.12 mol), m.p. 87° C.

EXAMPLE 9

In a 50 cc round-bottomed flask equipped with magnetic stirring, a thermometer, a condenser and a dropping funnel, there are introduced 1-chloroformyl-8-methyl-1,2,3,4-tetrahydro-4-quinoline (1.17 g; 5.2 mmol) and xylene (5 cc). The mixture is then heated by means of an oil bath maintained at 115° C. and 5N caustic soda (4 cc) is added. After 2 hours 40 minutes, the reaction mixture is cooled to 20° C. and methylene chloride (20 cc) and distilled water (20 cc) are added. The aqueous phase is separated by decantation and extracted with methylene chloride (4×10 cc). The combined organic extracts are washed with water (2×20 cc) and then dried over sodium sulphate. After filtration, the filtrate is concentrated to dryness under reduced pressure (20 mm Hg; 2.7 kPa) at 40° C. A yellow product (0.90 g) is obtained which melts between 86° C. and 88° C. The nuclear magnetic resonance spectrum shows that it is 8-methyl-1,2,3,4-tetrahydro-4-quinolinone containing 10% of impurities. After recrystallisation in hexane, the product melts at 98° C.

The structure of the 8-methyl-1,2,3,4-tetrahydro-4-quinolinone is confirmed by the infrared, mass and proton nuclear magnetic resonance spectra.

EXAMPLE 10

7-Chloro-1-chloroformyl-2-methyl-1,2,3,4-tetrahydro-4-quinolinone is prepared in a manner similar to that described in Example 5 but starting from 3-(3-chloroanilino)butanoic acid (5.42 g; 25.4 mmol), phosgene (6.7 g; 67.7 mmol), methylene chloride (25 cc), dimethylformamide (0.23 cc) and aluminum chloride (8.15 g; 61.1 mmol).

A white product (4.79 g), m.p. 132° C., is thus obtained. Analysis of the infrared, mass and nuclear magnetic resonance spectra shows that it is almost pure 7-chloro-1-chloroformyl-2-methyl-1,2,3,4-tetrahydro-4-quinolinone in which no 5-chloro-1-chloroformyl-2-methyl-1,2,3,4-tetrahydro-4-quinolinone is observed.

After recrystallisation in a toluene/hexane mixture (50:50 by volume), the product melts at 134° C.

3-(3-Chloroanilino)butanoic acid is prepared in a manner similar to that described in Example 1, but starting from 3-chloroaniline (65 cc; 0.5 mol), crotonic acid (11.20 g; 0.129 mol) and distilled water (31 cc). After purification, a product (14.66 g; 68.6 mmol) is thus obtained in the form of a white powder which melts at about 50° C.

EXAMPLE 11

7-Chloro-2-methyl-1,2,3,4-tetrahydro-4-quinolinone is prepared in a manner similar to that described in Example 4, but starting from 5-chloro-1-chloroformyl- 2-methyl-1,2,3,4-tetrahydro-4-quinolinone (1.30 g; 5.0 mmol), xylene (5 cc) and 5N caustic soda (4 cc).

A yellow product (1.08 g) is thus obtained which melts at between 155° C. and 160° C. Analysis of the infrared, mass and nuclear magnetic reasonance spectra shows that it is almost pure 7-chloro-2-methyl-1,2,3,4-tetrahydro-4-quinolinone in which no 5-chloro-2-methyl-1,2,3,4-tetrahydro-4-quinolinone is observed.

After recrystallisaton in a hexane/toluene mixture (50:50 by volume), the product melts at 168° C.

We claim:

1. A process for the preparation of a 1,2,3,4-tetrahydro-4-quinolinone of the formula:

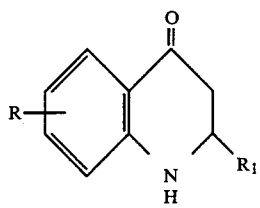

in which R denotes a hydrogen atom, a halogen atom, a linear or branched alkyl group of 1 to 4 carbon atoms or a linear or branched alkoxy group of 1 to 4 carbon atoms, and $R_1$ denotes a hydrogen atom or a linear or branched alkyl group of 1 to 4 carbon atoms, which comprises treating a 3-anilinopropinoic acid of the formula:

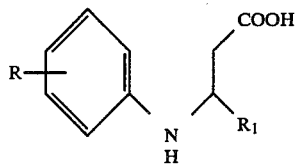

in which R and $R_1$ are as defined above, with phosgene to produce a product of the formula:

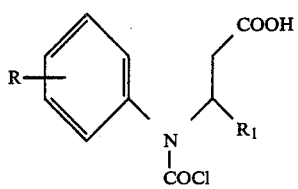

in which R and $R_1$ are as defined above, reacting the said product with phosgene in the presence of dimethylformamide, to produce an acid chloride of the formula:

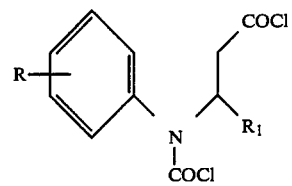

in which R and $R_1$ are as defined above, treating the latter with a aluminum chloride in a suitable solvent to provide a product of formula:

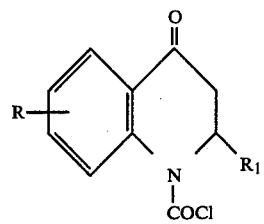

in which R and $R_1$ are as defined above, and hydrolysing the latter in the presence of an inert inorganic base to provide the 1,2,3,4-tetrahydro-4-quinolinone.

2. A process according to claim 1, in which the treatment with phosgene is performed in an organic solvent at a temperature between −10° and 150° C.

3. A process according to claim 2, in which the solvent is methylene chloride, 1,1,2-trichloroethane or dioxane.

4. A process according to claim 1, in which the hydrolysis is effected with sodium hydroxide in methanol.

5. A process according to claim 1, in which the product of formula:

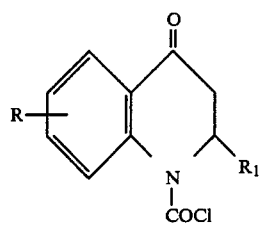

in which R and $R_1$ are as defined in claim 1, is prepared without isolation of the intermediate products.

6. A 1-chloroformyl-1,2,3,4-tetrahydro-4-quinolinone of the formula:

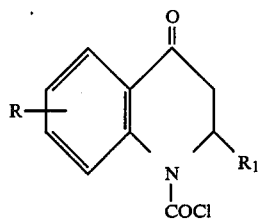

in which R and $R_1$ are as defined in claim 1 provided that when $R_1$ is a hydrogen atom and R is other than a chlorine, bromine or fluorine atom in position 6.

7. A process according to claim 1, in which the aluminum chloride is used in a solvent chosen from a halogenated hydrocarbon, carbon disulphide, a nitroalkane and tetrachloroethylene.

* * * * *